US008814944B2

(12) United States Patent
Hartdegen et al.

(10) Patent No.: US 8,814,944 B2
(45) Date of Patent: *Aug. 26, 2014

(54) TIBIAL IMPLANT BASE

(71) Applicant: Wright Medical Technology, Inc., Arlington, TN (US)

(72) Inventors: Vernon R. Hartdegen, Collierville, TN (US); David Robert Tuttle, Memphis, TN (US); John Michael Green, II, Arlington, TN (US)

(73) Assignee: Microport Orthopedics Holdings Inc., Tiel (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/659,264

(22) Filed: Oct. 24, 2012

(65) Prior Publication Data

US 2013/0046385 A1    Feb. 21, 2013

Related U.S. Application Data

(63) Continuation of application No. 12/574,009, filed on Oct. 6, 2009.

(51) Int. Cl.
*A61F 2/38* (2006.01)

(52) U.S. Cl.
USPC ..................................................... 623/20.32

(58) Field of Classification Search
USPC ................................ 623/20.15, 20.28, 20.32
See application file for complete search history.

(56) References Cited

U.S. PATENT DOCUMENTS

| 4,963,152 | A | 10/1990 | Hofmann et al. |
| 5,282,866 | A * | 2/1994 | Cohen et al. ............... 623/20.34 |
| 5,344,460 | A | 9/1994 | Turanyi et al. |
| 5,683,470 | A | 11/1997 | Johnson et al. |
| 5,702,463 | A | 12/1997 | Pothier et al. |
| 5,702,464 | A | 12/1997 | Lackey et al. |

(Continued)

FOREIGN PATENT DOCUMENTS

| EP | 0672397 | 6/2000 |
| EP | 0809986 | 10/2002 |
| EP | 2042134 | 4/2009 |
| WO | WO2011043955 | 4/2011 |

OTHER PUBLICATIONS

International Search Report and Written Opinion of International Application No. PCT/US2010/050497 filed Sep. 28, 2010 of Wright Medical Technology, Inc.

(Continued)

*Primary Examiner* — Bruce E Snow
*Assistant Examiner* — Brian Dukert
(74) *Attorney, Agent, or Firm* — Duane Morris LLP

(57) ABSTRACT

An orthopedic prosthesis includes a tibial implant and a tibial insert. The tibial implant includes an upper surface, a medial side, a lateral side and a first locking structure provided on the upper surface where the medial side and the lateral side of the tibial implant are defined by a medial-lateral midline. The tibial insert includes a second locking structure provided on its bottom surface. The first and second locking structures are configured for engaging each other along an engagement direction vector when the tibial insert is inserted into the tibial base towards the posterior side. The engagement direction vector is angled away from the medial-lateral midline of the tibial implant towards the medial side of the tibial implant by a predetermine angle.

20 Claims, 7 Drawing Sheets

(56) References Cited

U.S. PATENT DOCUMENTS

| | | | |
|---|---|---|---|
| 5,782,925 | A | 7/1998 | Collazo et al. |
| 5,964,808 | A | 10/1999 | Blaha et al. |
| 6,013,103 | A | 1/2000 | Kaufman et al. |
| 6,126,692 | A | 10/2000 | Robie et al. |
| RE37,277 | E | 7/2001 | Baldwin et al. |
| 6,379,388 | B1 * | 4/2002 | Ensign et al. ............ 623/20.34 |
| 6,893,463 | B2 | 5/2005 | Fell et al. |
| 2005/0055102 | A1 | 3/2005 | Tornier et al. |
| 2005/0283251 | A1 | 12/2005 | Coon et al. |
| 2008/0114464 | A1 | 5/2008 | Barnett et al. |
| 2009/0088859 | A1 | 4/2009 | Hazebrouck et al. |
| 2011/0082559 | A1 | 4/2011 | Hartdegen et al. |

OTHER PUBLICATIONS

U.S. Appl. No. 12/574,009 Official Office Action dated May 5, 2011.
U.S. Appl. No. 12/574,009 Official Office Action dated Nov. 8, 2011.
U.S. Appl. No. 12/574,009 Official Office Action dated Nov. 14, 2011.
U.S. Appl. No. 12/574,009 Official Office Action dated Apr. 27, 2012.
U.S. Appl. No. 12/574,009 Official Office Action dated Jul. 24, 2012.
U.S. Appl. No. 12/574,009 Official Office Action dated Oct. 10, 2012.
U.S. Appl. No. 12/574,009 Official Office Action dated Mar. 26, 2013.

* cited by examiner

TIBIAL IMPLANT BASE

CROSS-REFERENCE TO RELATED APPLICATIONS

This application is a continuation of U.S. patent application Ser. No. 12/574,009, filed Oct. 6, 2009, the entirety of which is herein incorporated by reference.

FIELD OF THE INVENTION

The present disclosure relates to orthopedic prostheses utilized in knee joint replacements.

BACKGROUND

Joint replacement surgery is well known in the art. It has provided many individuals near-normal joint function when it otherwise would not be possible to do so. Artificial joints usually comprise metallic, ceramic and/or plastic components that are fixed to existing bone. For example, knee arthroplasty is a well known surgical procedure by which a diseased and/or damaged natural knee joint is replaced with a prosthetic knee joint. A surgeon typically affixes two prosthesis components to the patient's femur and tibia. These replacement components are typically known as the femoral component and the tibial component. The femoral component is placed on a patient's distal femur after the surgeon makes a plurality of surgical cuts. A common type of tibial prosthesis uses a laterally extending base that is shaped to conform to the patient's proximal tibia after the proximal tibia has been cut transversely by the surgeon. The tibia prosthesis also includes a stem or plug that extends generally perpendicular or angled slightly to the base and from the center of the tibial base. The stem is placed in a surgically formed opening that extends into the patient's intramedullary canal from the transverse cut formed on the proximal tibia. A plastic, polymeric insert is attached to the tibial base. This insert provides a tibial articulating surface that articulates with the femoral articulating surface as the patient's tibia moves through a full range of motion with respect to the patient's femur.

SUMMARY

According to one embodiment of the present disclosure, an orthopedic prosthesis comprises a tibial implant comprising an upper surface, a medial side, a lateral side and a first locking structure provided on the upper surface. The medial side and the lateral side of the tibial implant are defined by a medial-lateral midline. The orthopedic prosthesis further includes a tibial insert comprising a bottom surface and a second locking structure provided on the bottom surface. The first and second locking structures are configured for engaging each other along an engagement direction vector when the tibial insert is inserted into the tibial base towards the posterior side. The engagement direction vector is angled away from the medial-lateral midline of the tibial implant towards the medial side of the tibial implant by a predetermined angle.

According to another embodiment, a tibial implant for an orthopedic prosthesis comprises an upper surface, a medial side, a lateral side, and a peripheral edge. The medial side and the lateral side of the tibial implant are defined by a medial-lateral midline. The peripheral edge has an anterior portion and a posterior portion. A first shoulder is provided along the posterior portion of the peripheral edge and projects upwardly from the upper surface. The first shoulder has an interior surface sloping inwardly and provides an undercut structure. A guide member extends from the first shoulder towards the anterior portion along an engagement direction vector. The engagement direction vector is angled away from the medial-lateral midline towards the medial side of the tibial implant by a predetermined angle and the guide member guides the tibial insert along the engagement direction vector when the tibial insert is inserted into the tibial base from medial side of the medial-lateral midline towards the posterior side.

The orthopedic prosthesis assembly of the present disclosure allows the tibial insert to be inserted into the tibial base from the medial side during an MIS (minimally invasive surgery) knee arthroplasty, thus minimizing the obstruction from the patient's patella.

BRIEF DESCRIPTION OF THE DRAWINGS

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
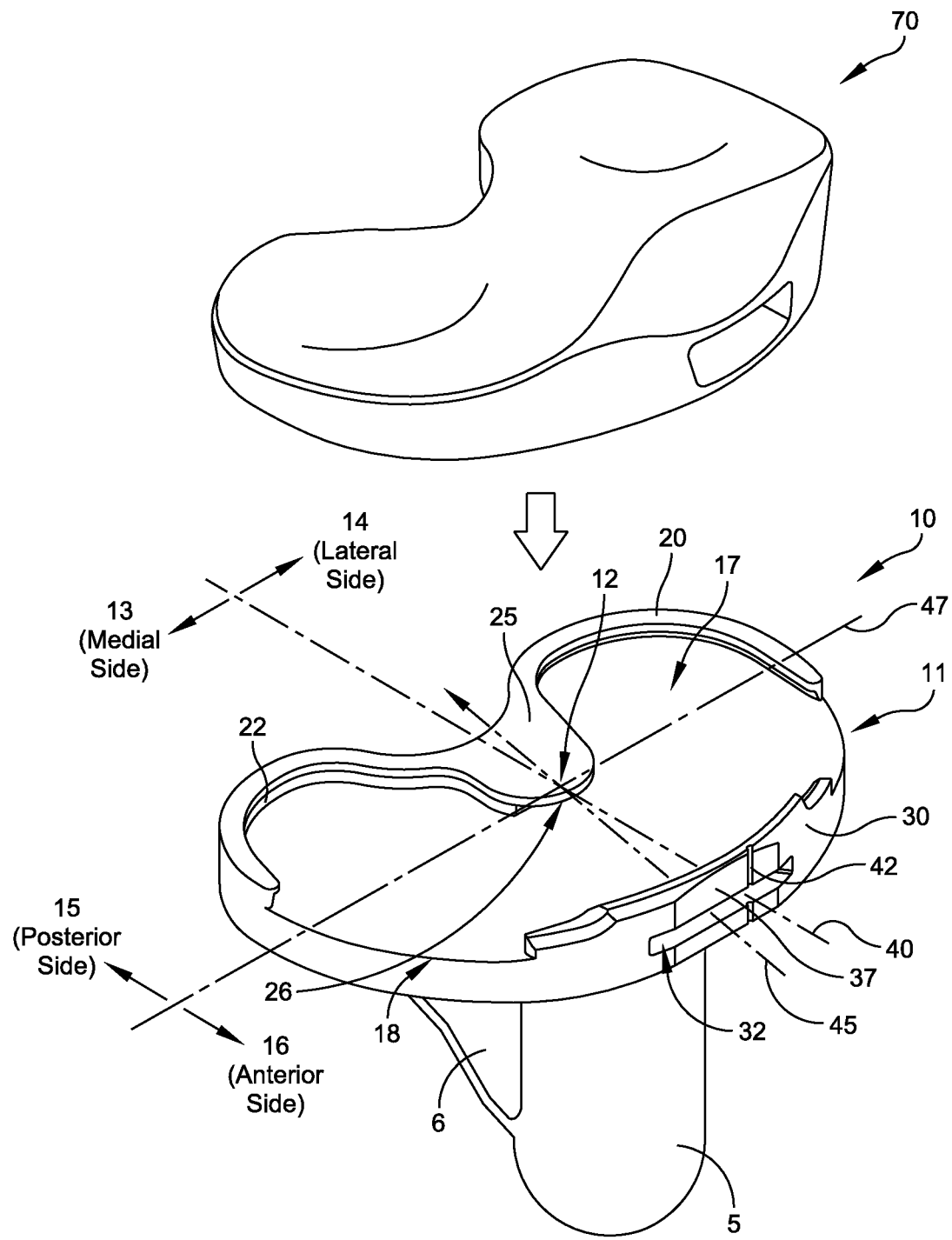
FIG. 1 is a perspective view of a tibial implant and a tibial insert assembly according to an embodiment of the present disclosure.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

FIGS. 1-4 show a tibial implant 10 and a corresponding tibial insert 70 of knee prosthesis according to an embodiment of the present disclosure. The tibial implant 10 comprises a tibial base 11 and a stem 5 provided on the bottom surface of the tibial base 11. The tibial base 11 is generally planar and has an outline that is intended to substantially match the cross-sectional outline of the proximal end of a tibial bone of a patient that has been prepared to receive the tibial implant 10.

The stem 5 includes a medial-posterior web 6 and a lateral-posterior web 7 each projecting outwardly from the stem 5. Each web 6 and 7 includes a wider upper portion at the end proximal to the tibial base 11 and a relatively narrower portion at the distal end of stem 5. The webs 6 and 7 are shaped to generally follow the internal contour of the central canal of the tibia to maximize contact with the cancellous bone in the central canal. The stem 5 may be configured to receive a stem extension member (not shown) at its distal end if necessary.

Figure 2:
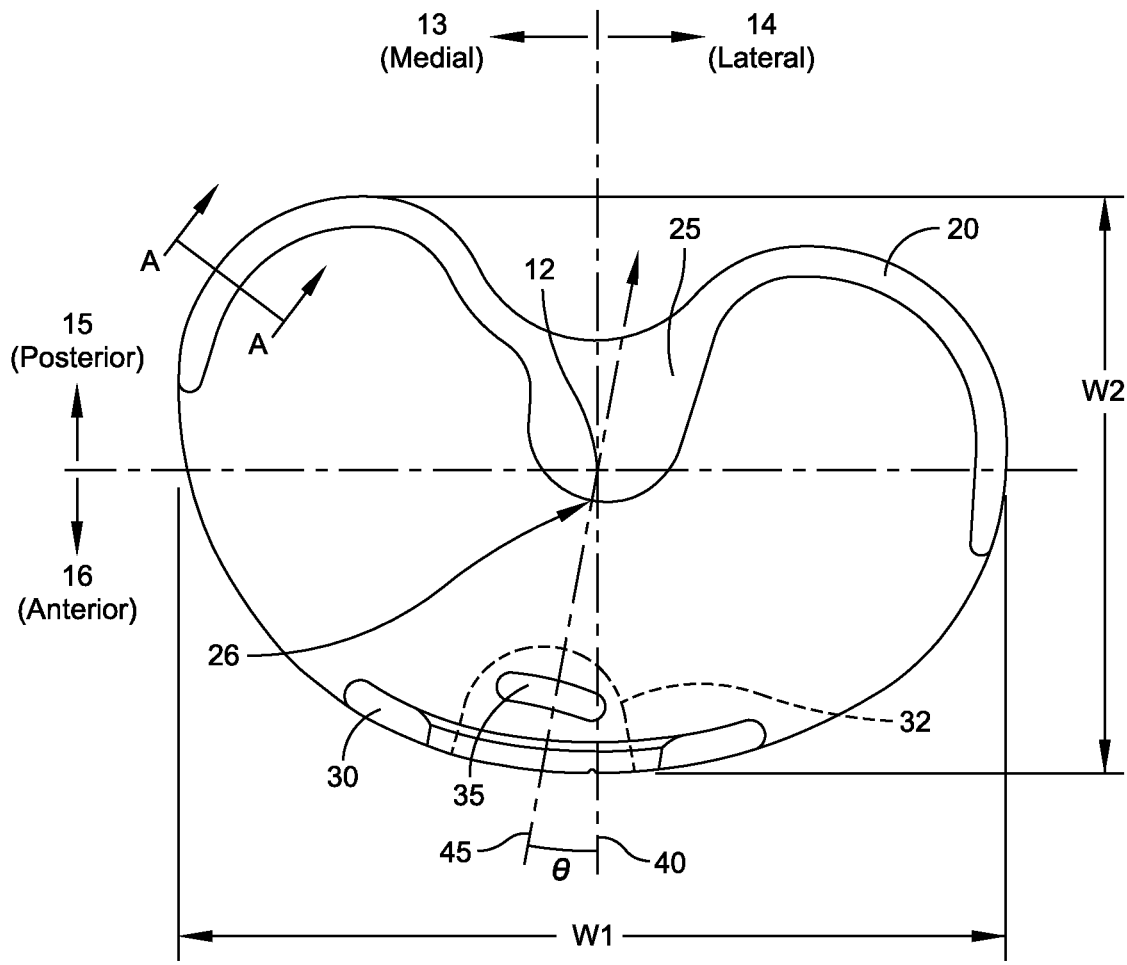
FIG. 2 is a plan view of the upper surface of the tibial implant of FIG. 1.

Referring to FIGS. 1 and 2, the tibial base 11 can be defined into a medial side 13 and a lateral side 14 by a sagittal plane going through the center 12 of the tibial base 11 along a medial-lateral midline 40. The tibial base 11 is further defined into a posterior side 15 and an anterior side 16 by a coronal plane going through the center 12 along an anterior-posterior midline 47. The center 12 of the tibial base 11 is defined as the midpoint of the width W1 of the tibial base 11 in the medial-lateral direction and the midpoint of the width W2 of the tibial base 11 in the anterior-posterior direction.

Figure 3:
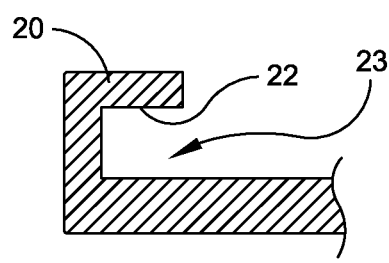
FIG. 3 is a cross-sectional view of a portion of a first shoulder provided on the tibial implant taken through the line A-A in FIG. 2.
Figure 4:
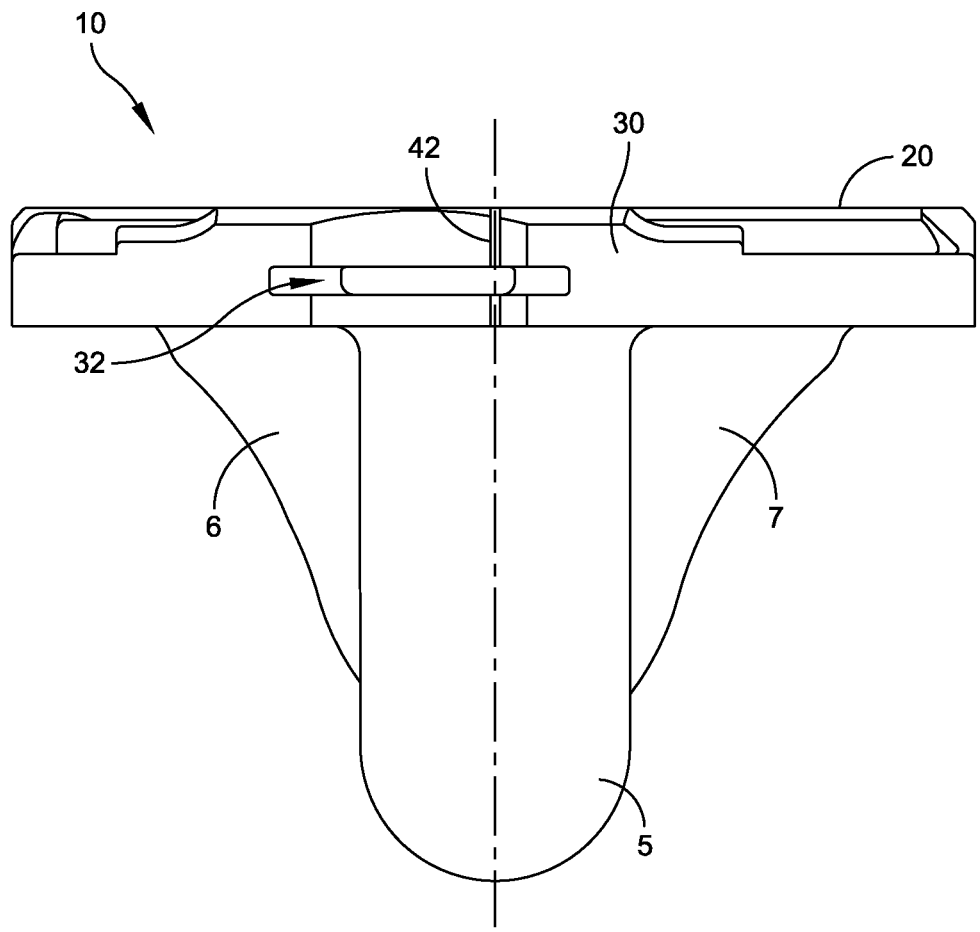
FIG. 4 is an anterior view of the tibial implant of FIG. 1.

The tibial base 11 comprises a substantially planar upper surface 17 and a peripheral edge 18 outlining the tibial base 11. The peripheral edge 18 has an anterior portion that is in the anterior side 16 of the tibial base 11 and a posterior portion that is in the posterior side 15 of the tibial base 11. The tibial base 11 includes a first shoulder 20 provided along the peripheral edge 18 substantially along the posterior portion of the peripheral edge 18. The first shoulder 20 projects upwardly from the upper surface 17 and includes an interior surface 22 that forms an undercut structure 23 along the interior side of the first shoulder 20. FIG. 3 is a cross-sectional view of the first shoulder 20 through the line A-A in FIG. 2 showing the undercut structure 23.

The tibial base 11 also comprises a second shoulder 30 provided along a segment of the anterior portion of the peripheral edge 18 and projecting upwardly from the upper surface 17 of the tibial base 11. The second shoulder 30 is configured for locking the tibial insert 70 into the tibial base 11 when the tibial insert 70 is fully inserted and seated into the tibial base 11. The first shoulder 20 and the second shoulder 30 of the tibial base 11 together form a locking structure on the tibial base 11 for engaging and locking with the tibial insert 70 by cooperating with a second locking structure provided on the bottom of the tibial insert 70.

As shown in FIG. 1, a marking, such as a notch 42, is provided on the anterior face 37 of the tibial base 11 marking the medial-lateral midline 40. During an MIS knee arthroplasty, when the tibial implant 10 is being implanted into a patient's tibia, the surgeon can use the notch 42 as a guide to orient the tibial base 11 in the anterior-posterior direction. When the tibial base 11 is properly positioned in the patient's tibia, the notch 42 is right behind the patient's patella.

After the tibial base 11 is positioned in the tibia, the tibial insert 70 is introduced through an incision in the patient's knee and inserted into the tibial base 11. The tibial insert 70 in inserted into the tibial base 11 and locked together by the first and second locking structures.

Figure 5:
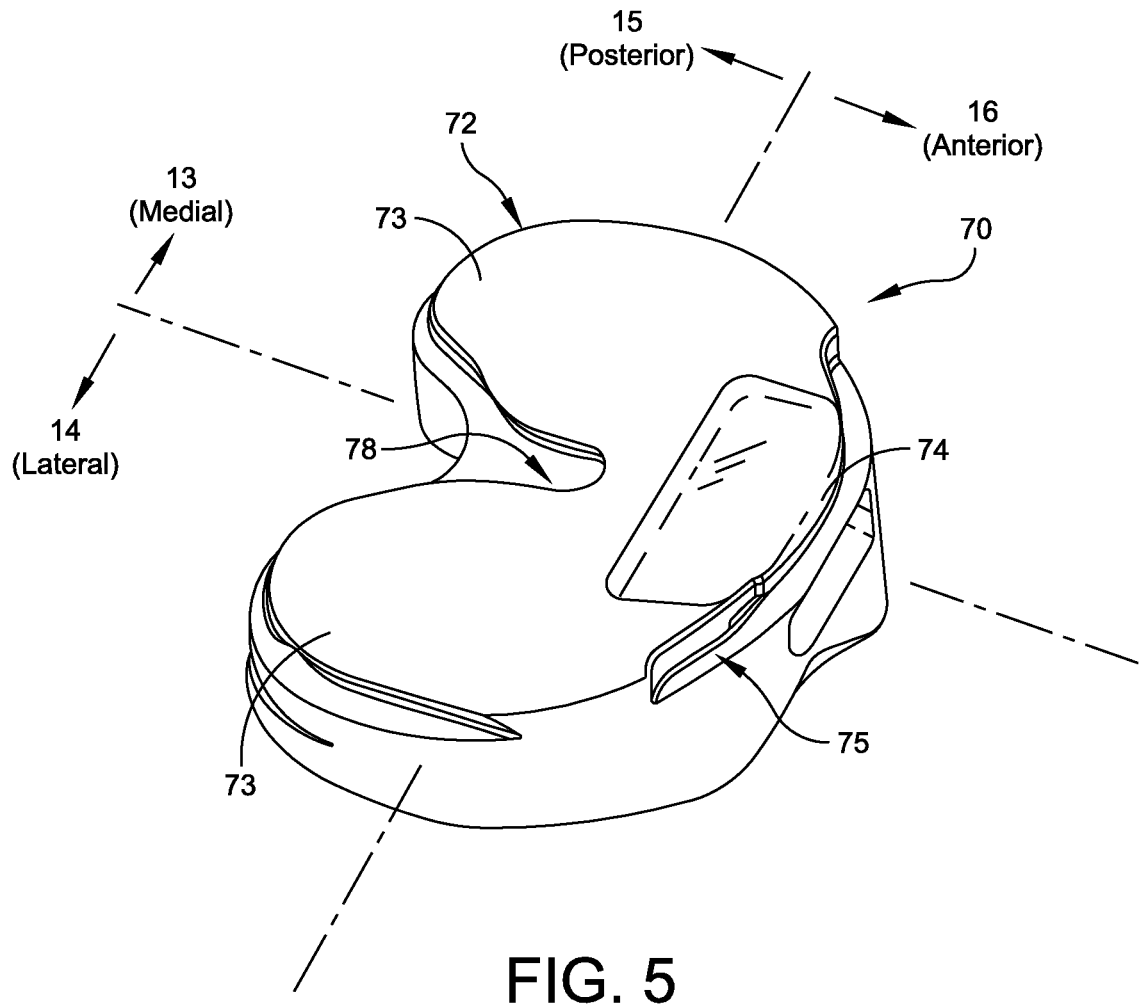
FIG. 5 is an isometric view of the tibial insert of FIG. 1 showing the bottom surface of the tibial insert.

The bottom of the tibial insert 70 is configured with a second locking structure that engages and cooperates with the first locking structure of the tibial base 11 for locking the tibial insert 70 to the tibial base 11 together. FIG. 5 is a perspective view of the bottom surface of the tibial insert 70 illustrating the second locking structure. Along the posterior edge 72 of the tibial insert 70, a lip 73 is provided for engaging the first shoulder 20 of the tibial base 11. The lip 73 has a curved shape following the outline of the posterior portion of the tibial insert 70 that also matches the curved shape of the first shoulder 20 of the tibial base 11.

The anterior edge 74 of the tibial insert 70 is configured to receive and engage the second shoulder 30 of the tibial base 11. The anterior edge 74 of the tibial insert 70 may be provided with a recessed region 75 providing a clearance space for accommodating the second shoulder 30. The recessed region 75 and the second shoulder 30 are configured to provide mechanical interference fit sufficient to keep the tibial insert 70 locked with the tibial base 11. However, the mechanical interference fit can be undone to remove the tibial insert 70 from the tibial 11 if necessary.

For example, in the illustrated example, the second shoulder 30 is provided with a lip 33 and the recessed region 75 of the tibial insert 70 is provided with a corresponding lip 74. When the tibial insert 70 is fully seated into the tibial base 11, these two lipped structures 33 and 74 snap-fit to lock the tibial insert 70 in the tibial base 11. The tibial base 11 is generally made from metal alloy suitable for implant in human body such as surgical grade titanium alloy or cobalt chrome alloy and the tibial insert 70 is generally made from a softer polymer-based material and thus facilitate the snap-fit locking between the tibial insert 70 and the tibial base 11.

During an MIS procedure, the insertion of the tibial insert 70 described above is accomplished from the anterior side of the patient through an incision. However, in conventional tibial implant systems, the insertion and locking of the tibial insert into the tibial base is accomplished along the medial-lateral midline 40. But because the patient's patella is in the anterior side of the patient's knee directly along the medial-lateral midline 40, the insertion procedure for the tibial insert in a conventional tibial implant system can be problematic.

Figure 6:
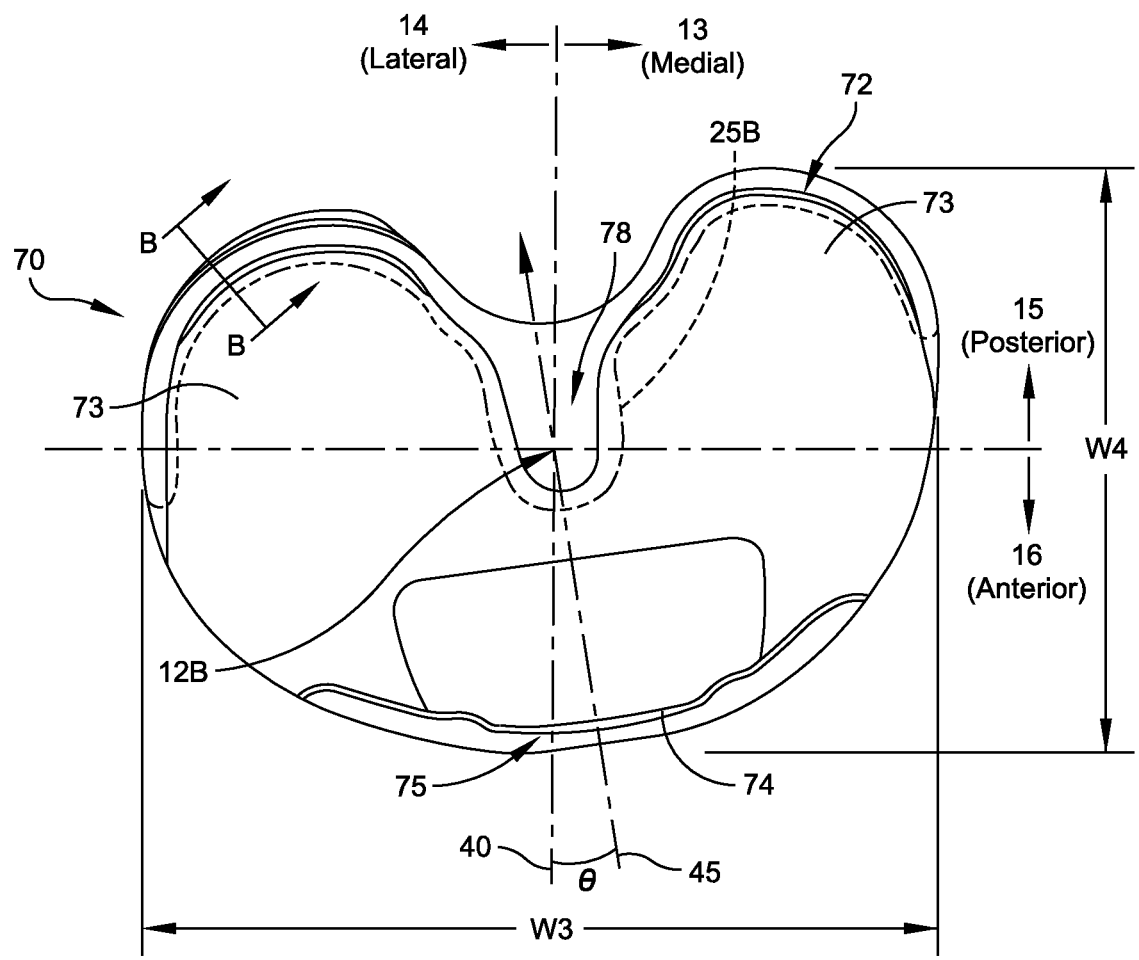
FIG. 6 is a bottom-up view of the bottom surface of the tibial insert of FIG. 5.

Referring to FIGS. 2 and 6, according to an embodiment of the present disclosure, the tibial insert 70 and the tibial base 11 are configured so that the tibial insert 70 is inserted into the tibial base 11 along an engagement direction vector 45 that is angled away from the medial-lateral midline 40 towards the medial side 13 at a predetermined angle θ. The predetermined angle θ can be about 3 degrees up to about 45 degrees and in one embodiment the angle θ is about 8 degrees. This enables the surgeon to insert the tibial insert 70 from the medial side of the medial-lateral midline 40 and avoid the interference from the patella.

To facilitate the engagement of the tibial insert 70 and the tibial base 11 along the engagement direction vector 45, the first shoulder 20 of the tibial base 11 includes a guide member 25 that extends from the first shoulder 20 for guiding the direction of the engagement between the tibial insert 70. The guide member 25 extends from the first shoulder 20 towards the anterior along the engagement direction vector 45. The posterior edge 72 of the tibial insert 70 is provided with a guide pocket 78 for receiving and engaging the guide member 25. The guide pocket 78 has an elongated shape that also extends in the direction along the engagement direction vector 45. The guide pocket 78 is formed by a looping portion of the lip 73 provided along the posterior edge 72 and is configured to receive and straddle the guide member 25 and guide the direction of the engagement of the tibial insert 70 with the tibial base 11 along the engagement direction vector 45. In FIG. 6, the dotted-line outline 25B illustrates the outline of the guide member 25 engaged underneath the edge of the lip 73 when the tibial insert 70 and the tibial base 11 are fully engaged and seated. Thus, the tibial insert 70 can be inserted from the anterior-medial side of the patella bone during an MIS procedure avoiding the obstruction by the patient's patella.

Referring to FIG. 2, the engagement direction vector 45 is defined by the predetermined angle θ with respect to the medial-lateral midline 40. The guide member 25 extends from the first shoulder 20 along the engagement direction vector 45. Although the engagement direction vector 45 is shown as intersecting the medial-lateral midline 40 at the center 12 in FIG. 2, this is not a necessity. The engagement direction vector 45 merely defines the direction of engagement between the tibial base 11 and the tibial insert 70. Thus, actual location of the guide member 25 in a given tibial implant 10 need not be aligned over the center 12 as long as the guide member 25 extends from the first shoulder 20 along a direction parallel to the engagement direction vector 45 to enable the tibial insert 70 to be inserted into the tibial base 11 from the medial side.

Referring to FIG. 6, the guide pocket 78 provided on the bottom surface of the tibial insert 70 extends along in the direction parallel to the engagement direction vector 45 mirroring the orientation of the guide member 25. Because the bottom surface of the tibial insert 70 engage the upper surface of the tibial base 11, the engagement direction vector 45 shown in FIGS. 2 and 6 are the mirror images of each other. Also, similar to the location of the center 12 of the tibial base 11, the center 12B of the tibial insert 70 is defined as the midpoint of the width W3 of the tibial insert 70 in the medial-lateral direction and the midpoint of the width W3 of the tibial insert 70 in the anterior-posterior direction. When the tibial insert 70 is inserted and fully seated in the tibial base 11, the centers 12 and 12B align with one another.

Again, as mentioned above with respect to the guide member 25, although the guide pocket 78 is shown as being located over the center 12B in FIG. 6, the illustrated figure is only an example a configuration for the second locking structure provided on the bottom surface of the tibial insert 70 and the actual location of the guide pocket 78 and the corresponding guide member 25 in a given prosthesis do not need to be aligned over the center 12 of the tibial base 11 and the center 12B of the tibial insert 70 as long as they are aligned with one another and oriented in a direction parallel to the engagement direction vector 45. In other words, the peripheral outlines of the tibial insert 70 and the tibial base 11 may remain unchanged (in turn, their dimensions, W1, W2, W3 and W4) but the location of the guide pocket 78 and the corresponding guide member 25 can change with respect to the peripheral outlines of the tibial insert 70 and the tibial base 11 and the guide pocket 78 and the guide member 25 will always be oriented such that they engage each other along a direction parallel to the engagement direction vector 45.

Figure 7:
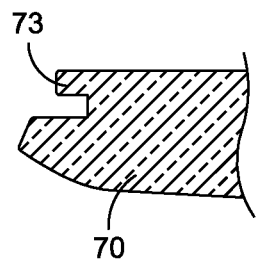
FIG. 7 is a sectional view of the tibial insert taken through the line B-B in FIG. 6.

FIG. 7 shows a cross-sectional view of the tibial insert 70 taken through the line B-B in FIG. 6. FIG. 7 shows the profile of the lip 73 provided for engaging the first shoulder 20 of the tibial base 11.

Figure 9:
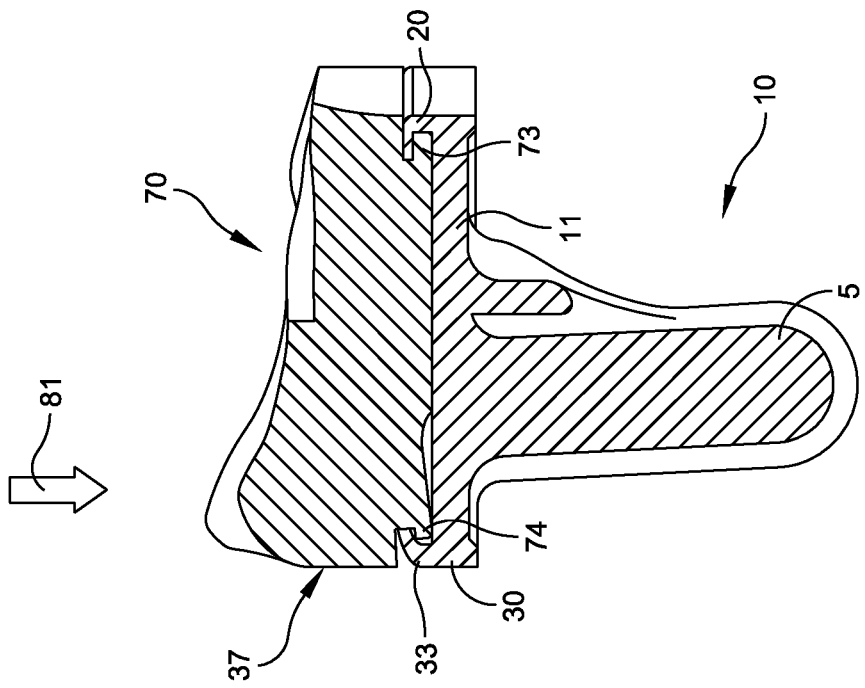
FIG. 9 is a cross-section side view of the tibial implant and tibial insert assembly post-lock state, wherein the section is taken through the line C-C of FIG. 10.
Figure 8:
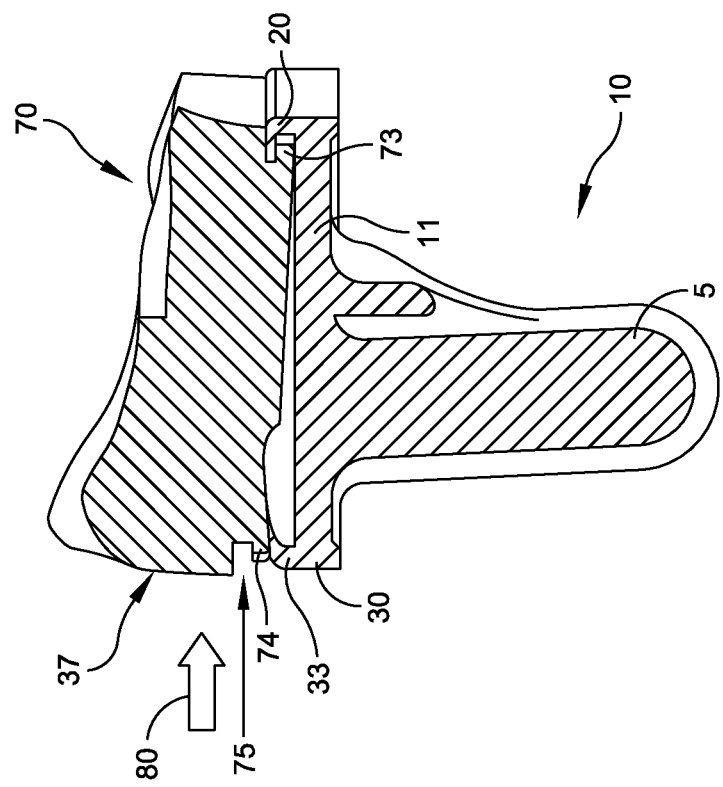
FIG. 8 is a cross-section side view of the tibial implant and tibial insert assembly in a pre-lock state, wherein the section is taken through the line C-C in FIG. 10.
Figure 10:
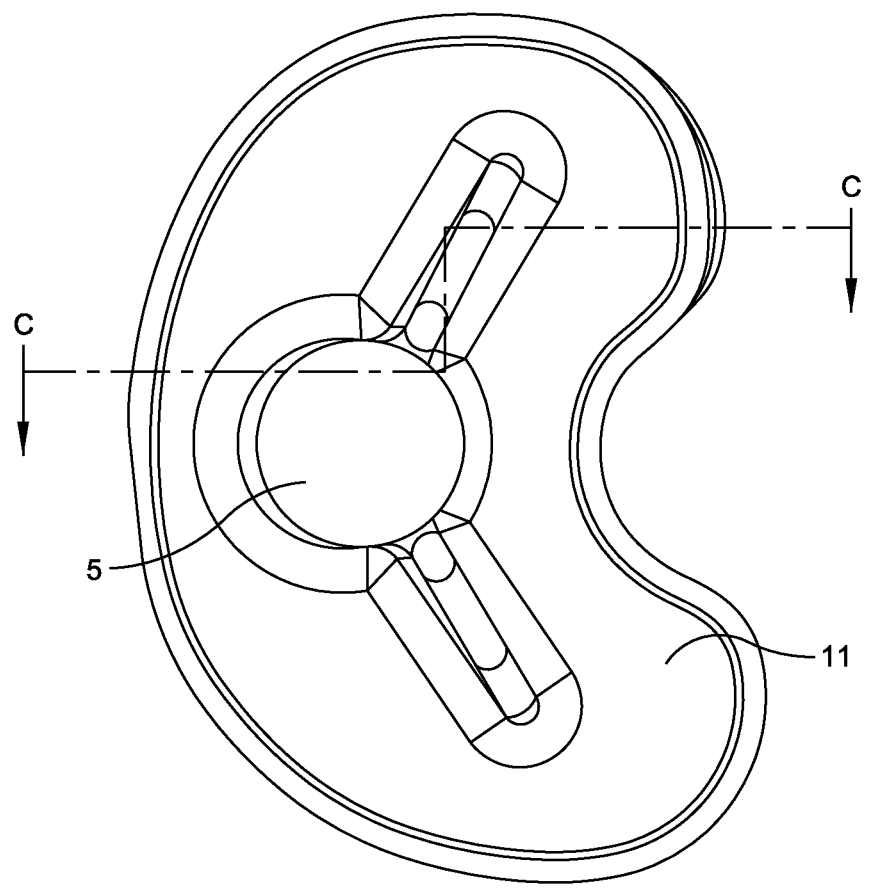
FIG. 10 is a view of the tibial implant and tibial insert assembly of FIG. 1 from the bottom side of the tibial implant showing the sectional line C-C.

FIGS. 8 and 9 show cross-sectional side views of the tibial implant 10 and tibial insert 70 assembly in a pre-lock state and a post-lock state, respectively, as the tibial insert 70 is inserted into the tibial base 10. The posterior edge 72 of the tibial insert 70 is first lowered into the posterior side 15 of the tibial base 11 allowing the lip 73 of the tibial insert 70 to engage the undercut structure 23 of the first shoulder 20. Then, the tibial insert 70 is pushed toward the posterior direction 80 until the second shoulder 30 of the tibial base 11 is aligned with the recessed region 75 of the tibial insert 70. Then, the anterior end of the tibial insert 70 is pushed downward 81 until the lip 74 of the tibial insert 70 and the lip 33 of the second shoulder 30 are forced over each other forming a snap-fit locking engagement and fully seating the tibial insert 70 in the tibial implant 10. The step of pushing the tibial insert 70 downward and snap-fitting it may be accomplished by an appropriate tool to provide a sufficient force. FIG. 10 shows the sectional line C-C through which the cross-sectional views of FIGS. 8 and 9 are taken.

The tibial base 11 may be configured to allow the tibial insert 70 to be unlocked. As shown in FIGS. 1 and 2, the tibial base 11 is provided with a cavity 32 accessible from the anterior surface 37. On the upper surface of the tibial base 11, a slot 35 is provided that opens into the cavity 32. In order to unlock the tibial insert 70 from the tibial base 11, an appropriate unlocking tool is inserted into the cavity 32 and push the tibial insert 70 upwards through the slot 35, thus, unlocking the tibial insert 70 from the tibial base 11.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention. The scope of the invention disclosed herein is to be limited only by the following claims.

What is claimed is:

1. An orthopedic prosthesis, comprising:
   a stem;
   a tibial base coupled to an end of the stem, the tibial base including
   an upper surface, a medial side, a lateral side, an anterior side, a posterior side, a peripheral edge including an anterior portion, and a posterior portion, the medial side and the lateral side being defined by a medial-lateral midline and the anterior side and the posterior side being defined by an anterior-posterior midline,
   a first locking structure including first and second shoulders, the first shoulder projecting upwardly from the upper surface of the tibial base to define a first undercut structure disposed along the posterior portion of the peripheral edge, the second shoulder projecting upwardly from the upper surface of the tibial base to define a second undercut structure disposed along the anterior portion of the peripheral edge, and
   a guide member extending from the first shoulder along an engagement direction vector; and
   a tibial insert including a medial bearing surface, a lateral bearing surface, a bottom surface, and a second locking structure provided on the bottom surface,
   wherein the guide member is configured to guide the tibial insert along the engagement direction vector when the tibial insert is inserted into the tibial base towards the posterior side, the first and second locking structures are configured for engaging each other to lock the tibial insert to the tibial base when the tibial insert is fully seated in the tibial base, and the engagement direction vector is angled away from the medial-lateral midline of the tibial base towards the medial side of the tibial base by a predetermine angle.

2. The orthopedic prosthesis of claim 1, wherein the predetermined angle is about 8 degrees.

3. The orthopedic prosthesis of claim 1, wherein the predetermined angle is about 3 to 45 degrees.

4. The orthopedic prosthesis of claim 1, wherein the second undercut is configured to receive a lip of the tibial insert for locking the tibial insert to the tibial base when the tibial insert is fully seated.

5. The orthopedic prosthesis of claim 1, wherein the second locking structure comprises:
a posterior locking ledge provided on the bottom surface of the tibial insert, the posterior locking ledge configured for engaging the first undercut, wherein the first shoulder of the tibial base and the posterior locking ledge of the tibial insert are configured to engage each other along the engagement direction vector.

6. The orthopedic prosthesis of claim 5, wherein the posterior locking ledge is provided with a pocket portion, said pocket portion being positioned and aligned to engage the guide member along the engagement direction vector.

7. The orthopedic prosthesis of claim 1, wherein the anterior side of the tibial base defines a cavity sized and configured to receive an unlocking tool for unlocking the tibial insert from the tibial base.

8. The orthopedic prosthesis of claim 7, wherein the anterior side of the tibial base includes a notch for assisting a surgeon with orienting the tibial base in an anterior-posterior direction.

9. A tibial implant, comprising:
a stem from which at least one web outwardly extends; and
a tibial base coupled to an end of the stem, the tibial base including
an upper surface, a medial side, a lateral side, an anterior side, a posterior side, a peripheral edge including an anterior portion, and a posterior portion, the medial side and the lateral side being defined by a medial-lateral midline and the anterior side and the posterior side being defined by an anterior-posterior midline,
a first locking structure including first and second shoulders, the first shoulder projecting upwardly from the upper surface of the tibial base to define a first undercut structure disposed along the posterior portion of the peripheral edge, the second shoulder projecting upwardly from the upper surface of the tibial base to define a second undercut structure disposed along the anterior portion of the peripheral edge, and
a guide member extending from the first shoulder along an engagement direction vector,
wherein the guide member is configured to guide a tibial insert along the engagement direction vector when the tibial insert is inserted into the tibial base towards the posterior side, the first locking structure is configured to engage a second locking structure of the tibial insert to lock the tibial insert to the tibial base when the tibial insert is fully seated in the tibial base, and the engagement direction vector is angled away from the medial-lateral midline of the tibial base towards the medial side of the tibial base by a predetermine angle.

10. The tibial implant of claim 9, wherein the predetermined angle is about 8 degrees.

11. The tibial implant of claim 9, wherein the predetermined angle is about 3 to 45 degrees.

12. The tibial implant of claim 9, wherein the second undercut is configured to receive a lip of the tibial insert for locking the tibial insert to the tibial base when the tibial insert is fully seated.

13. The tibial implant of claim 9, wherein the second locking structure includes
a posterior locking ledge provided on the bottom surface of the tibial insert, the posterior locking ledge configured for engaging the first undercut, wherein the first shoulder of the tibial base and the posterior locking ledge of the tibial insert are configured to engage each other along the engagement direction vector.

14. The tibial implant of claim 13, wherein the posterior locking ledge is provided with a pocket portion, said pocket portion being positioned and aligned to engage the guide member along the engagement direction vector.

15. The tibial implant of claim 9, wherein the anterior side of the tibial base defines a cavity sized and configured to receive an unlocking tool for unlocking a tibial insert from the tibial base.

16. The tibial implant of claim 15, wherein the anterior side of the tibial base includes a notch for assisting a surgeon with orienting the tibial base in an anterior-posterior direction.

17. An implant, comprising:
a stem from which a medial-posterior web and a lateral-posterior web outwardly extend;
a tibial base coupled to an end of the stem, the tibial base including
an upper surface, a medial side, a lateral side, an anterior side, a posterior side, a peripheral edge including an anterior portion, and a posterior portion, the medial side and the lateral side being defined by a medial-lateral midline and the anterior side and the posterior side being defined by an anterior-posterior midline,
a first shoulder projecting upwardly from the upper surface of the tibial base to define a first undercut structure disposed along the posterior portion of the peripheral edge,
a second shoulder projecting upwardly from the upper surface of the tibial base to define a second undercut structure disposed along the anterior portion of the peripheral edge, and
a guide member extending from the first shoulder along an engagement direction vector; and
a tibial insert including a medial bearing surface, a lateral bearing surface, a bottom surface, and a second locking structure provided on the bottom surface,
wherein the guide member is configured to guide the tibial insert along the engagement direction vector when the tibial insert is inserted into the tibial base towards the posterior side, the first and second shoulders are configured for engaging structures on the tibial insert to lock the tibial insert to the tibial base when the tibial insert is fully seated in the tibial base, and the engagement direction vector is angled away from the medial-lateral midline of the tibial base towards the medial side of the tibial base by a predetermine angle.

18. The implant of claim 17, wherein the predetermined angle is about 8 degrees.

19. The implant of claim 17, wherein the predetermined angle is about 3 to 45 degrees.

20. The implant of claim 17, wherein the tibial insert includes
a lip for engaging the second undercut of the tibial base, and
a posterior locking ledge provided on the bottom surface of the tibial insert for engaging the first undercut of the tibial base.

* * * * *